United States Patent [19]
Andree et al.

[11] 3,987,189
[45] Oct. 19, 1976

[54] ANTI-INFLAMMATORY COMPOSITION AND METHOD CONTAINING CYCLIC 2-FURFURAL-ACETALS

[75] Inventors: Hans Andree, Dusseldorf-Itter; Christian Gloxhuber, Haan Rhld.; Hinrich Möller, Dusseldorf-Benrath; Ferdi Saygin, Erkrath Rhld., all of Germany

[73] Assignee: Henkel & Cie G.m.b.H., Dusseldorf-Holthausen, Germany

[22] Filed: June 11, 1974

[21] Appl. No.: 478,342

[30] Foreign Application Priority Data
June 22, 1973 Germany............................ 2331821

[52] U.S. Cl............................ 424/285; 260/340.7; 260/340.9; 424/DIG. 5; 424/47; 424/59; 424/73; 424/168
[51] Int. Cl.²......................................... A61K 31/34
[58] Field of Search................. 424/285, 59, 278

[56] References Cited
UNITED STATES PATENTS
3,682,973   8/1972   Eriksoo et al...................... 424/278

OTHER PUBLICATIONS
Mattor et al., 1966, vol. 64, pp. 1511 and 1512, Chemical Abstracts.
Pastor et al., Chem. Abstracts, 1966, vol. 65, pp. 5430 and 5431.
Ciba Ltd., Chem. Abstracts, 1968, vol. 68, p. 49617z.
Chuche et al., Chem. Abs., 1968, vol. 69, p. 27295m.
Ap'ok et al., Chem. Abs. 1969, vol. 70, p. 47374k.

*Primary Examiner*—Dale R. Ore
*Attorney, Agent, or Firm*—Hammond & Littell

[57] ABSTRACT

Anti-inflammatory cyclic 2-furfural-acetals of the formula

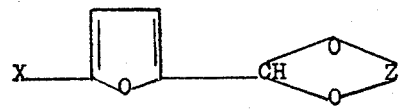

in which X is hydrogen, a lower alkyl preferably having 1 to 4 carbon atoms, or nitro, Z is an alkylene of the formula

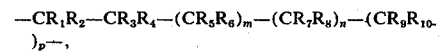

in which $R_1$ to $R_6$ are, independently of one another, hydrogen, alkyl having 1 to 26 carbon atoms, hydroxyalkyl, or aryl, $R_7$ to $R_{10}$ are independently of one another, hydrogen or lower alkyl preferably having 1 to 4 carbon atoms, $R_1$ and $R_3$ or $R_1$ and $R_5$ may, together with their associated carbon atom, represent a carbocyclic ring system with 5 to 8 carbon atoms, and $m$, $n$ and $p$ are 0 or 1, as used in cosmetic preparations for the prevention and control of inflammation, and methods for the prevention and control of inflammation.

8 Claims, No Drawings

ANTI-INFLAMMATORY COMPOSITION AND METHOD CONTAINING CYCLIC 2-FURFURAL-ACETALS

OBJECTS OF THE INVENTION

An object of the present invention is the obtaining of an anti-inflammatory cosmetic preparation consisting essentially of from 0.01% to 10% by weight of an anti-inflammatory cyclic 2-furfural-acetal compound having the formula

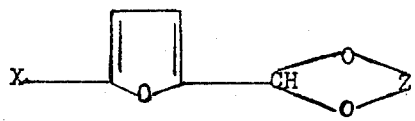

wherein X is selected from the group consisting of hydrogen, lower alkyl and nitro, Z is alkylene having the formula

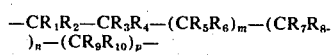

wherein $R_1$, $R_2$, $R_3$, $R_4$, $R_5$ and $R_6$ are each selected from the group consisting of hydrogen, alkyl having 1 to 26 carbon atoms, hydroxyalkyl having 1 to 26 carbon atoms and phenyl, and wherein $R_7$, $R_8$, $R_9$ and $R_{10}$ are each selected from the group consisting of hydrogen and lower alkyl, and wherein $R_1$ and $R_3$ or $R_1$ and $R_5$ taken together are alkylene having 3 to 6 carbon atoms, and $m$, $n$ and $p$ are each the integer 0 or 1; and the remainder inert cosmetic excipients.

It is another object of the present invention to provide a process for the prevention or alleviation of inflammation of the skin consisting essentially of applying to the skin to be protected a safe but effective amount of the above-described anti-inflammatory cyclic 2-furfural-acetal compound.

It is a further object of the present invention to provide an anti-inflammatory cyclic 2-furfural-acetal compound having the formula

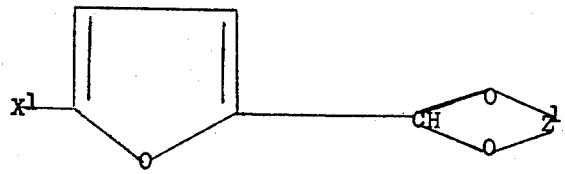

wherein $X^1$ is selected from the group consisting of hydrogen, methyl and nitro, $Z^1$ is alkylene having the formula

wherein $R_1$, $R_2$, $R_3$, $R_4$, $R_5$ and $R_6$ are each selected from the group consisting of hydrogen, methyl, isopropyl, propyl, dodecyl, tetradecyl and hexadecyl, and $R_1$ and $R_3$ taken together are alkylene having 4 carbon atoms, A. provided that whenever $X^1$ is hydrogen, $R_1$ and $R_3$ taken together are alkylene having 4 carbon atoms, or $R_1$, $R_2$, $R_3$, $R_4$, $R_5$ and $R_6$ are each selected from the group consisting of hydrogen, methyl and isopropyl, with the proviso that at least two of $R_1$, $R_2$, $R_3$, $R_4$, $R_5$ and $R_6$ must be other than hydrogen;

B. provided that whenever $X^1$ is methyl, $R_1$, $R_2$, $R_3$, $R_4$, $R_5$ and $R_6$ are each selected from the group consisting of hydrogen, methyl and isopropyl, with the proviso that at least three of $R_1$, $R_2$, $R_3$, $R_4$, $R_5$ and $R_6$ must be other than hydrogen, and C. provided that whenever $X^1$ is nitro, $R_1$ and $R_3$ taken together are alkylene having 4 carbon atoms or $R_1$, $R_2$, $R_3$, $R_4$, $R_5$ and $R_6$ are each selected from the group consisting of hydrogen, methyl, propyl, dodecyl, tetradecyl and hexadecyl, with the proviso that if anyone of $R_1$, $R_2$, $R_3$, $R_4$ $R_5$ and $R_6$ is selected from the group consisting of dodecyl, tetradecyl and hexadecyl, then all the other of $R_1$, $R_2$, $R_3$, $R_4$, $R_5$ and $R_6$ must be hydrogen, with the proviso that if anyone of $R_1$, $R_2$, $R_3$, $R_4$, $R_5$ and $R_6$ is selected from the group consisting of methyl or propyl, then at least one other of $R_1$, $R_2$, $R_3$, $R_4$, $R_5$ and $R_6$ must be selected from the group consisting of methyl and propyl with the remainder of $R_1$ to $R_6$ being hydrogen, and with the proviso that at least one of $R_1$, $R_2$, $R_3$, $R_4$, $R_5$ and $R_6$ is always other than hydrogen, and wherein $m$ is the integer 0 or 1.

A yet further object of the present invention is the development of processes for the preparation of anti-inflammatory cyclic 2-furfural-acetal compounds.

These and other objects of the invention will become apparent as the description thereof proceeds.

DESCRIPTION OF THE INVENTION

The present invention relates to inflammation preventatives for use in cosmetic preparations, especially for compositions for protection against the sun and sunburn control, based on cyclic 2-furfural-acetals.

It has been found that cyclic 2-furfural-acetals of the formula:

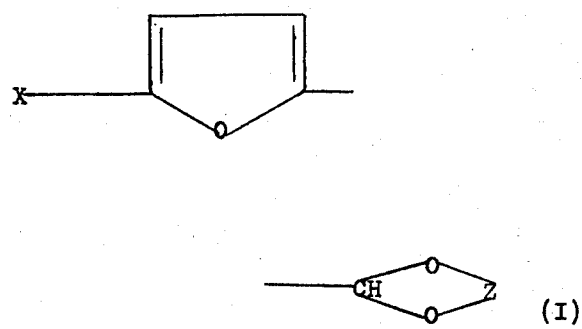

in which X is hydrogen, a lower alkyl, preferably having 1 to 4 carbon atoms, or nitro, Z is an alkylene of the formula:

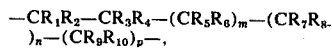

in which $R_1$ to $R_6$ are, independently of one another, hydrogen alkyl having 1 to 26 carbon atoms, hydroxyalkyl, or aryl, $R_7$ to $R_{10}$ are independently of one another, hydrogen or lower alkyl preferably having 1 to 4 carbon atoms, $R_1$ and $R_3$ or $R_1$ and $R_5$ may, together with their associated carbon atom, represent a carbocyclic ring system with 5 to 8 carbon atoms, and $m$, $n$ and $p$ are 0 or 1, are outstandingly suitable as inflammation preventatives for use in cosmetic preparations.

More particularly, the present invention provides an anti-inflammatory cosmetic preparation consisting essentially of from 0.01% to 10% by weight of an anti-inflammatory cyclic 2-furfural-acetal compound having the formula

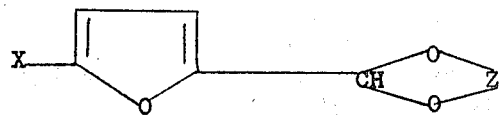

wherein X is selected from the group consisting of hydrogen, lower alkyl and nitro, Z is alkylene having the formula

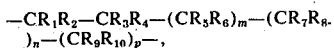

wherein $R_1$, $R_2$, $R_3$, $R_4$, $R_5$ and $R_6$ are each selected from the group consisting of hydrogen, alkyl having 1 to 26 carbon atoms, hydroxyalkyl having 1 to 26 carbon atoms and phenyl, and wherein $R_7$, $R_8$, $R_9$ and $R_{10}$ are each selected from the group consisting of hydrogen and lower alkyl, and wherein $R_1$ and $R_3$ or $R_1$ and $R_5$ taken together are alkylene having 3 to 6 carbon atoms, and $m$, $n$ and $p$ are each the integer 0 or 1; and the remainder inert cosmetic excipients.

Preferably, the present invention is directed to an anti-inflammatory cosmetic preparation, as described above, wherein X is selected from the group consisting of hydrogen, methyl and nitro, wherein $R_1$, $R_2$, $R_3$, $R_4$, $R_5$ and $R_6$ are each selected from the group consisting of hydrogen, methyl, ethyl, propyl, isopropyl, butyl, hexyl, octyl, decyl dodecyl, tetradecyl, hexadecyl and phenyl, wherein $R_7$ and $R_8$ are each selected from the group consisting of hydrogen and methyl, and $R_1$ and $R_3$ or $R_1$ and $R_5$ taken together are alkylene having 4 carbon atoms; and wherein $m$ and $n$ are each the integer 0 or 1.

The present invention further provides a process for the prevention or alleviation of inflammation of the skin consisting essentially of applying to the skin to be protected a safe but effective amount of the anti-inflammatory cyclic 2-furfural-acetal compound, as described above.

Some of the anti-inflammatory cyclic 2-furfural-acetal compounds are, in addition, novel compounds. Among these novel compounds are those cyclic 2-furfural-acetal compounds having the formula

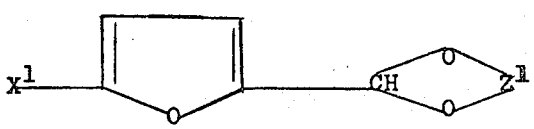

wherein $X^1$ is selected from the group consisting of hydrogen, methyl and nitro, $Z^1$ is alkylene having the formula

wherein $R_1$, $R_2$, $R_3$, $R_4$, $R_5$ and $R_6$ are each selected from the group consisting of hydrogen, methyl, isopropyl, propyl, dodecyl, tetradecyl and hexadecyl, and $R_1$ and $R_3$ taken together are alkylene having 4 carbon atoms, A. provided that whenever $X^1$ is hydrogen, $R_1$ and $R_3$ taken together are alkylene having 4 carbon atoms, or $R_1$, $R_2$, $R_3$, $R_4$, $R_5$ and $R_6$ are each selected from the group consisting of hydrogen, methyl and isopropyl, with the proviso that at least two of $R_1$, $R_2$, $R_3$, $R_4$, $R_5$ and $R_6$ must be other than hydrogen;

B. provided that whenever $X^1$ is methyl, $R_1$, $R_2$, $R_3$, $R_4$, $R_5$ and $R_6$ are each selected from the group consisting of hydrogen, methyl and isopropyl, with the proviso that at least three of $R_1$, $R_2$, $R_3$, $R_4$, $R_5$ and $R_6$ must be other than hydrogen and C. provided that whenever $X^1$ is nitro, $R_1$ and $R_3$ taken together are alkylene having 4 carbon atoms or $R_1$, $R_2$, $R_3$, $R_4$, $R_5$ and $R_6$ are each selected from the group consisting of hydrogen, methyl, propyl, dodecyl, tetradecyl and hexadecyl, with the proviso that if anyone of $R_1$, $R_2$, $R_3$, $R_4$, $R_5$ and $R_6$ is selected from the group consisting of dodecyl, tetradecyl and hexadecyl, then all the other of $R_1$, $R_2$, $R_3$, $R_4$, $R_5$ and $R_6$ must be hydrogen, with the proviso that if anyone of $R_1$, $R_2$, $R_3$, $R_4$, $R_5$ and $R_6$ is selected from the group consisting of methyl or propyl, then at least one other of $R_1$, $R_2$, $R_3$, $R_4$, $R_5$ and $R_6$ must be selected from the group consisting of methyl and propyl with the remainder of $R_1$ to $R_6$ being hydrogen, and with the proviso that at least one of $R_1$, $R_2$, $R_3$, $R_4$, $R_5$ and $R_6$ is always other than hydrogen and $m$ is the integer 0 or 1.

Examples of these novel cyclic 2-furfural acetals are as follows:

2-(5'-nitrofuryl-2')-5-methyl-5-propyl-1, 3-dioxane,
2-(5'-nitrofuryl-2')-4,4,5,5-tetramethyl-1,3-dioxolane,
2-(5'-nitrofuryl-2')-4,5-tetramethylene-1,3-dioxolane,
2-(furyl-2')-4-isopropyl-5,5-dimethyl-1,3-dioxane,
2-(furyl-2'-4,5-dimethyl-1,3-dioxolane,
2-(5'-methylfuryl-2')-4-isopropyl-5,5-dimethyl-1,3-dioxane,
2-(5'-methylfuryl-2')-4,5-dimethyl-1,3-dioxolane,
2-(5'-nitrofuryl-2')-4,5,6-trimethyl-1,3-dioxane,
2-(5'-nitrofuryl-2')-4,4,6-trimethyl-1,3-dioxane,
2-(5'-nitrofuryl-2')-4-dodecyl-1,3-dioxolane,
2-(5'-nitrofuryl-2')-4-tetradecyl-1,3-dioxolane,
2-(5'-nitrofuryl-2')-4-hexadecyl-1,3-dioxolane,
2-(5'-nitrofuryl-2')-4,6-dimethyl-1,3-dioxane, and
2-(furyl-2')-4,5-tetramethylene-1,3-dioxolane.

All of the cyclic 2-furfural-acetal compounds of Formula I above are of very special importance as inflammation-preventing substances in compositions for protection of the skin against the sun and for sunburn control, since, in addition to an excellent anti-inflammatory action, they also have a good absorption action with respect to ultra-violet radiation.

The preparation of the cyclic 2-furfural-acetals to be used according to the invention may be effected by known methods by acid condensation of a furfural of the formula

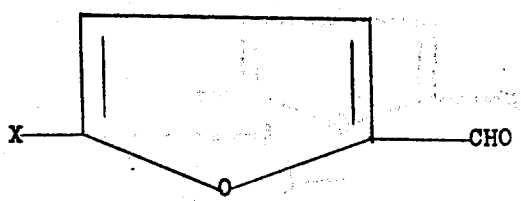

with a substantially equimolar amount of an alkanediol of the formula

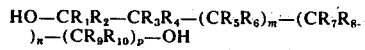

in which X, $R_1$ to $R_{10}$, and m, n and p have the same meanings as defined above. The water formed in the reaction may be separated with an inert solvent, as for example benzene, in a water trap or be chemically bound with a stoichiometric amount of polyphosphoric acid. In the first case the catalyst utilized is, for example, p-toluenesulfonic acid, ferric chloride, calcium chloride, zinc chloride, pyridine hydrochloride or phosphoric acid. The furfural-acetals can also be prepared by reaction of the corresponding furfural with diols in the presence of orthoformic acid-trialkyl esters and acid catalysts.

According to a further process cyclic 5-nitro-2-furfural-acetals can be prepared especially by reaction of the 5-nitro-2-furfural-diacetate with a molar excess such as 2 to 3 mols of the above-mentioned alkanediols in the presence of an effective amount of acid catalysts, preferably p-toluenesulfonic acid. The water formed in the reaction is centrifuged out with an inert organic solvent. This process often provides higher yields and has the advantage that one can start directly from 5-nitro-2-furfural-diacetate, from which 5-nitro-furfural is otherwise prepared.

Compounds to be used according to the invention are, for example:

2-(5'-nitrofuryl-2')-1,3-dioxolane,
2-(5'-nitrofuryl-2')-1,3-dioxepane,
2-(5'-nitrofuryl-2')-5-methyl-5-propyl-1,3-dioxane,
2-(5'-nitrofuryl-2')-4,4,5,5-tetramethyl-1,3-dioxolane,
2-(5'-nitrofuryl-2')-4,5-tetramethylene-1,3-dioxolane,
2-(5'-nitrofuryl-2')-4,5,6-trimethyl-1,3-dioxane,
2-(5'-nitrofuryl-2')-4,4,6-trimethyl-1,3-dioxane,
2-(5'-nitrofuryl-2')-4-dodecyl-1,3-dioxolane,
2-(5'-nitrofuryl-2')-4-tetradecyl-1,3-dioxolane,
2-(5'-nitrofuryl-2')-4-hexadecyl-1,3-dioxolane,
2-(5'-nitrofuryl-2')-4,6-dimethyl-1,3-dioxane,
2-(5'-nitrofuryl-2')-4-methyl-1,3-dioxolane,
2-(5'-nitrofuryl-2')-4,5-dimethyl-1,3-dioxolane,
2-(5'-nitrofuryl-2')-4-butyl-1,3-dioxolane,
2-(5'-nitrofuryl-2')-4-hexyl-1,3-dioxolane,
2-(5'-nitrofuryl-2')-4-octyl-1,3-dioxolane,
2-(5'-nitrofuryl-2')-4-decyl-1,3-dioxolane,
2-(5'-nitrofuryl-2')-4-isopropyl-5,5-dimethyl-1,3-dioxane,
2-(5'-nitrofuryl-2')-4-methyl-1,3-dioxane,
2-(5'-nitrofuryl-2')-1,3-dioxane,
2-(5'-nitrofuryl-2')-4,5-diphenyl-1,3-dioxolane,
2-(5'-nitrofuryl-2')-4-phenyl-5,5-diethyl-1,3-dioxane,
2-(5'-nitrofuryl-2')-4-phenyl-1,3-dioxolane,
2-(5'-nitrofuryl-2')-4-phenyl-1,3-dioxane,
2-(5'-nitrofuryl-2')-5-ethyl-5-n-butyl-1,3-dioxane,
2-(furyl-2')-4-isopropyl-5,5-dimethyl-1,3-dioxane,
2-(furyl-2')-4,5-dimethyl-1,3-dioxolane,
2-(furyl-2')-4,5-tetramethylene-1,3-dioxolane,
2-(5'-methylfuryl-2')-4-i-propyl-5,5-dimethyl-1,3-dioxane, and
2-(5'-methyl-furyl-2')-4,5-dimethyl-1,3-dioxolane.

The compounds to be used according to the invention are colorless to faintly yellow colored crystalline substances, which are marked by a good anti-inflammatory activities with good physiological compatibility. Since the absorption maxima of many of these compounds lies favorably in the ultra-violet region which produces erythema and which extends from 280 to 320 mμ, besides their favorable anti-inflammatory activity in cosmetic preparations such as sunburn control agents, they have proved at the same to be useful agents for protecting the skin against the sun.

When used as anti-inflammatory substances, the cyclic 2-furfural-acetals embraced by Formula I according to the invention may be incorporated in liquid, pasty or solid cosmetic preparations, as, for example, aqueous solutions, aqueous suspensions, emulsions, solutions in organic solvents, oils, salves, ointments, creams, pencils or powders. The preparations may serve a large variety of purposes, such as general skin cleansing lotions with an anti-inflammation action, shaving lotion, lotions, pencils or lotions against insect bites or stings, shaving powders, baby-powders, baby-creams or baby-lotions, but especially as aqueous, emulsion-like, oily or pasty compositions for protection against the sun or sunburn control compositions.

For use as anti-inflammation active compound, the cyclic 2-furfural-acetal embraced by Formula I according to the invention are used preferably in amounts from 0.01% to 10% by weight, especially 0.1% to 5% by weight, based upon the total weight of the cosmetic composition.

The following examples are merely illustrative of the present invention without being deemed limitative in any manner thereof.

EXAMPLE 1

2-(5'-Nitrofuryl-2')-1,3-dioxolane, Compound A.

A mixture of 24.3 gm (0.1 mol) of 5-nitro-furfuraldiacetate, 12.4 gm of ethyleneglycol, 0.3 gm of p-toluenesulfonic acid and 100 ml of benzene was heated at its boiling point under reflux for 8 hours in a water separator. After 3.4 ml of water had separated, the benzene solution was washed with dilute sodium bicarbonate solution and water, dried over calcium chloride and concentrated by evaporation. The residue was fractionally distilled in vacuo, 12.9 gm (70% of theory) of 2-(5'-nitrofuryl-2')-1,3-dioxolane, with a boiling point of 128° to 131° C at 0.8 mm Hg, being obtained. The melting point of the compound after recrystallization from ether/petroleum ether was 43 to 45° C.

EXAMPLE 2

Using a procedure analogous to that described in Example 1, 2-(5'-nitrofuryl-2')-1,3-dioxepane, Compound B, having a boiling point of 128° C at 0.4 mm Hg and a melting point of 45° to 46° C, was prepared from 5-nitro-furfuraldiacetate and butanediol-1,4.

EXAMPLE 3

Using a procedure analogous to that described in Example 1, 2-(5'-nitrofuryl-2')-5-methyl-5-propyl-1,3- dioxane, Compound C, having a melting point of 70° to 78° C, was prepared from 5-nitro-furfuraldiacetate and 2-methyl-2-propyl-propanediol-1,3, in a 55% yield, and having the formula

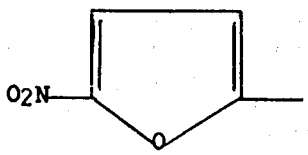

EXAMPLE 4

Using a procedure analogous to that described in Example 1, 2-(5'-nitrofuryl-2')-4,4,5,5-tetramethyl-1,3-dioxolane, Compound D, having a melting point of 110° to 120° C, was prepared from 5-nitro-furfuraldiacetate and 2,3-dimethylbutanediol-2,3, in a yield of 34%, and having the formula

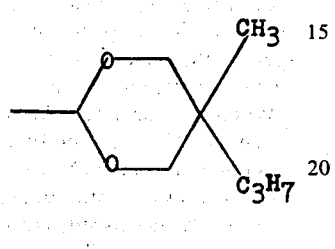

EXAMPLE 5

Using a procedure analogous to that described in Example 1, 2-(5'-nitrofuryl-2')-4,5-tetramethylene-1,3-dioxolane Compound E, having a boiling point of 140° to 157° C at 0.6 mm Hg and a melting point of 65° to 75° C, (recrystallized from methanol), was prepared from 5-nitro-furfuraldiacetate and cis, trans-1,2-cyclohexanediol, as a conformal mixture, in a yield of 42%, and having the formula

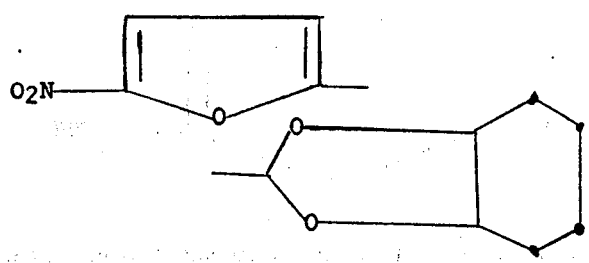

The molar ratio of 5-nitrofurfuraldiacetate to cis, trans-1,2-cyclohexanediol was 1:5.

EXAMPLE 6

2-(5'-Nitrofuryl-2')-4,5-tetramethylene-1,3-dioxolane, Compound E

A mixture of 20 gm (0.143 mol) of 5-nitrofurfural, 16.5 gm (0.143 mol) of 1,2-cyclohexanediol (cis/-trans), 15.1 gm (0.143 mol) orthoformic acid-trimethyl ester and 0.1 gm of ammonium chloride was stirred for 24 hours at room temperature. The readily volatile components were then distilled off up to a bath temperature of 90° C, and the remaining oily residue was taken up in benzene. After washing the water, drying with calcium chloride and distilling off the benzene, the residue was rectified and 8.4 gm (25% of theory) of 2-(5'-nitrofuryl-2')-4,5-tetramethylene-1,3-dioxolane were obtained. The boiling point was 133° to 143° C at 0.2 mm Hg. A considerable increase in yield was possible by the use of two to three times the stoichiometric amount of 1,2-cyclohexanediol.

EXAMPLE 7

Using a procedure analogous to that described in Example 6, 2-(furyl-2')-4-isopropyl-5,5-dimethyl-1,3-dioxane, Compound F, having a boiling point of 93° to 94° C at 0.5 mm Hg and $n_D^{20} = 1.4738$, was prepared from furfural and 2,4,4-trimethyl-pentanediol-3,5 in a yield of 78%.

EXAMPLE 8

Using a procedure analogous to that described above in Example 6, 2-(furyl-2')-4,5-dimethyl-1,3-dioxolane, Compound G, having a boiling point of 44° to 46° C at 0.1 mm Hg and $n_D^{20} = 1.4693$, was prepared from furfural and butanediol-2,3 in a yield of 82%.

EXAMPLE 9

Using a procedure analogous to that described in Example 6, 2-(5'-methylfuryl-2')-4-isopropyl-5,5-dimethyl-1,3-dioxane, Compound H, having a boiling point of 102° to 104° C at 0.4 mm Hg and $n_D^{20} = 1.4748$, was prepared from 5-methylfurfural and 2,4,4-trimethyl-pentanediol-3,5 in a yield of 81%, and having the formula

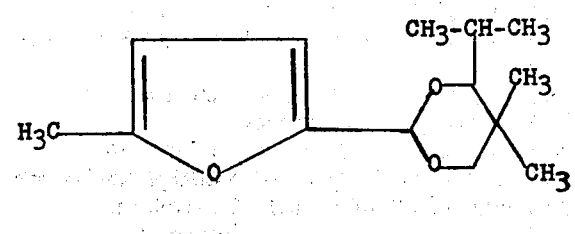

EXAMPLE 10

Using a procedure analogous to that described in Example 6, 2-(5'-methylfuryl-2')-4,5-dimethyl-1,3-dioxolane, Compound J, having a boiling point of 68° to 69° C at 0.1 mm Hg and $n_D^{20} = 1.4733$, was prepared from 5-methylfurfural and butanediol-2,3 in a yield of 85%.

EXAMPLE 11

2-(5'-Nitrofuryl-2')-4,5,6-trimethyl-1,3-dioxane, Compound K

A mixture of 28.2 gm (0.2 mol) of 5-nitrofurfural, 35.4 gm (0.2 mol) of 3-methyl-pentanediol-2,4 and 10 gm of polyphosphoric acid (76% $P_2O_5$) were stirred at 80° C for 3 hours. After cooling, the product was poured into ice/water and extracted with benzene. The benzene phase was washed until the washings were neutral, dried over calcium chloride, and the benzene was distilled off. The rectification of the residue gave 40.7 gm (85% of theory) of 2-(5'-nitrofuryl-2')-4,5,6-trimethyl-1,3-dioxane having a boiling point of 121° C at 0.05 mm Hg and $n_D^{20} = 1.5245$.

EXAMPLE 12

Using a procedure analogous to that described in Example 11, 2-(5'-nitrofuryl-2')-4,4,6-trimethyl-1,3-dioxane, Compound L, having a boiling point of 120° to 123° C at 0.05 mm Hg, was prepared from 5-nitrofurfural and 2-methylpentanediol-2,4, in a yield of 40%.

EXAMPLE 13

Using a procedure analogous to that described in Example 11, 2-(5'-nitrofuryl-2')-4-dodecyl-1,3-dioxolane, Compound M, having a melting point of 44° C, was prepared from 5-nitrofurfural and tetradecanediol-1,2.

EXAMPLE 14

Using a procedure analogous to that described in Example 11, 2-(5'-nitrofuryl-2')-4-tetradecyl-1,3-dioxolane, Compound N, having a melting point of 50° C, was prepared from 5-nitrofurfural and hexadecanediol-1,2.

EXAMPLE 15

Using a procedure analogous to that described in Example 11, 2-(5'-nitrofuryl-2')-4-hexadecyl-1,3-dioxolane, Compound O, having a melting point of 56° C, was prepared from 5-nitrofurfural and octadecanediol-1,2.

EXAMPLE 16

Using a procedure analogous to that described in Example 11, 2-(5'-nitrofuryl-2')-4,6-dimethyl-1,3-dioxane, Compound P, having a melting point of 90° to 91° C, was prepared from 5-nitrofurfural and pentanediol-2,4.

EXAMPLE 17

Using a procedure analogous to that described in Example 11, 2-(5'-nitrofuryl-2')-4-isopropyl-5,5-dimethyl-1,3-dioxane, Compound Q, having a boiling point of 110° to 112° C at 0.05 mm Hg and $n_D^{20} = 1.5124$, was prepared from 5-nitrofurfural and 2,4,4-trimethyl-pentanediol-3,5.

EXAMPLE 18

Using a procedure analogous to that described in Example 11, 2-(5'-nitrofuryl-2')-4-methyl-1,3-dioxolane, Compound R, having a boiling point of 114° to 115° C at 0.05 mm Hg and $n_D^{20} = 1.5297$, was prepared from 5-nitrofurfural and 1,2-propandiol.

EXAMPLE 19

Using a procedure analogous to that described in Example 11, 2-(5'-nitrofuryl-2')-4-n-butyl-1,3-dioxolane, Compound S, having a boiling point of 144° to 146° C at 0.05 mm Hg and $n_D^{20} = 1.5123$, was prepared from 5-nitrofurfural and 1,2-hexanediol.

EXAMPLE 20

Using a procedure analogous to that described in Example 11, 2-(5'-nitrofuryl-2')-4-n-hexyl-1,3-dioxolane, Compound T, having a boiling point of 150° C at 0.05 mm Hg and $n_D^{20} = 1.5045$, was prepared from 5-nitrofurfural and 1,2-octanediol.

EXAMPLE 21

Using a procedure analogous to that described in Example 11, 2-(5'-nitrofuryl-2')-4-n-octyl-1,3-dioxolane, Compound U, having a boiling point of 156° C at 0.01 mm Hg and $n_D^{20} = 1.5005$, was prepared from 5-nitrofurfural and 1,2-decanediol.

EXAMPLE 22

Using a procedure analogous to that described in Example 11, 2-(5'-nitrofuryl-2')-4-n-decyl-1,3-dioxolane, Compound V, having a melting point of 29° to 30° C, was prepared from 5-nitrofurfural and 1,2-dodecanediol.

EXAMPLE 23

Using a procedure analogous to that described in Example 11, 2-(5'-nitrofuryl-2')-1,3-dioxane, Compound W, having a melting point of 112°–113° C, was prepared from 5-nitrofurfural and 1,3-propanediol.

EXAMPLE 24

Using a procedure analogous to that described in Example 11, 2-(5'-nitrofuryl-2')-4-methyl-1,3-dioxane, Compound X, having a melting point of 109° to 110° C, was prepared from 5-nitrofurfural and 1,3-butanediol.

EXAMPLE 25

2-(Furyl-2')-4,5-tetramethylene-1,3-dioxolane, Compound Y

A mixture of 19.2 gm (0.2 mol) of furfural, 58.1 gm (0.5 mol) of 1,2-cyclo-hexanediol (cis/trans), 200 ml of benzene and 100 mgm of ammonium chloride was heated up to boiling until the water separation was completed. After the usual working up and distillation, 20 gm (51% of theory) of 2-(furyl-2')-4,5-tetramethylene-1,3-dioxolane of boiling point 74° to 77° C at 0.1 mm Hg and refractive index $n_{D20} = 1.5015$, were obtained.

Since the application of the cosmetic preparations is topical the dosage amounts of the anti-inflammatory cyclic 2-furfural-acetal compounds can vary widely.

A part of the above-mentioned furan derivatives are novel and have not previously been described in the literature, as discussed above.

The following shows the anti-inflammatory properties of the compounds to be used according to the invention, as well as their suitability for cosmetic preparations, especially compositions for protection against the sun and sunburn control compositions.

In the following experiments listed below the cyclic 2-furfural-acetals to be used according to the invention were tested for their anti-inflammatory properties. First an orienting experiment was carried out to determine their toxicity, in order to be able to determine the test dosages for the further experiments.

As a determination of the suitability of the compounds for preventing the inflammation caused by sunburn, a variation of the rats paw test was used, namely the so-called amputation method was used, which is described by C. H. Winter in the Journal of Pharmacology and Experimental Therapeutics 141, p.369 (1963). In the experiments, Carrageenin is used as the substance causing inflammation.

While only the Carrageenin solution was administered to the control animals, the test animals were given the different test substances by injection or by administration per os in the amount given in Table I below, 30 minutes before its injection with the Carrageenin solution. The test animals were killed 3 hours after the injection of the carrageenin solution causing the inflammation, and the weight of the paws was determined. The inhibiting of the development of the edema of the rats paws after the subplantar injection of the compound checking inflammation was used as an index of the degree of activity and was expressed in % inhibition.

On the basis of general practice, the results of the rats paw test serve as a base for the evaluation of a compound as a sunburn control agent.

In addition, the absorption maxima of the test substances in the ultraviolet region are given in the following Table I. Since with some of the test substances the absorption maxima lie conveniently in the ultraviolet region producing erythema, which extends from 280 to 320 m$\mu$ these, besides their inflammation-preventing action as sunburn control substances, show themselves simultaneously as useful means for protection from the sun.

In the previously described experiments, the values given in the following Table I were found for the individual substances.

TABLE 1

| Test Substance | Orienting toxicity $L_D50$ gm/kg | Rat's paw test with carrageenin induced edema | | UV-spectrum $\lambda$-max m$\mu$(log$\epsilon$) |
|---|---|---|---|---|
| | | Dosing mgm/kg | Checking % | |
| A | 0.81 | 500 p.o. | 16.2 | 302 (4.02) |
| B | 1.75 | 500 p.o. | 12.3 | — |
| C | 0.3 | 250 p.o. | 16.5 | 302 (3.98) |
| D | 0.81 | 500 p.o. | 16.5 | 303 (4.01) |
| E | 1.0 | 500 p.o. | 17.7 | 305 (4.01) |
| F | 0.3 | 250 p.o. | 48.4 | 300 (2.35) |
| G | 0.3 | 250 p.o. | 14.5 | 300 (2.13) |
| H | 1.0 | 1000 p.o. | 50.0 | 300 (2.08) |
| J | 1.0 | 1000 p.o. | 48.4 | 300 (1.96) |
| K | 0.69 | 250 p.o. | 30.8 | 303 (3.76) |
| L | 1.13 | 500 p.o. | 21.9 | 304 (4.01) |
| M | 1.0 | 1000 i.p. | 18.3 | — |
| N | 1.0 | 1000 i.p. | 10.5 | — |
| O | 2.5 | 250 i.p. | 29.6 | — |
| Q | 1.75 | 750 p.o. | 34.1 | 301 (4.07) |
| R | 0.75 | 50 i.p. | 36.6 | 303 (3.84) |
| S | 0.81 | 500 i.p. | 10.6 | — |
| T | 1.0 | 1000 p.o. | 12.8 | — |
| U | 5.0 | 250 i.p. | 17.0 | — |
| V | 1.0 | 1000 p.o. | 18.3 | — |
| W | 0.75 | 500 p.o. | 16.9 | 303 (3.79) |
| X | 0.75 | 500 p.o. | 12.1 | 303 (3.87) |
| Y | 0.3 | 250 p.o. | 32.3 | — | p.o. = orally,
i.p. = interperitoneally

The cosmetic preparations of the present invention, especially where sunburn preparations are concerned, may include a component which will impart suppleness to the skin and/or keep it from drying up as much as possible. Such a component is a fatty component, such as a derivative of a long chain fatty acid especially an ester thereof whose alcohol moiety is derived from a short- or long-chain mono- or multi-hydric alcohol.

Further the cosmetic preparations of the present invention may have a content of an emulsifying agent, for example one or more of a partial ester or soap of a long chain fatty acid, higher fatty alcohol natural wax, fat or oil and glycerine.

Specific examples of cosmetic preparations according to the present invention are as follows:

EXAMPLE 26

Suntan Oil

A suntan oil was prepared as follows:

20 gm of 2-(5'-nitrofuryl-2')-4-isopropyl-5,5-dimethyl-1,3-dioxane were heated while suspended in a very fine state in 100 gm of paraffin oil and then thoroughly mixed at about 25° C with the following other ingredients:

300 gm of vegetable oil containing lecithin
400 gm of olive oil
100 gm of isopropyl myristate, and
100 gm of purcellin oil.

EXAMPLE 27

Suntan Powder

A suntan powder was prepared as follows:

40 gm of 2-(furyl-2')-4-isopropyl-5,5-dimethyl-1,3-dioxane were introduced into a powder mixing appliance together with
400 gm of rice starch
400 gm of colloid clay
100 gm of lycopodium, and
100 gm of talcum,
and the mixture was intensively mixed to obtain a powder having a uniform distribution.

EXAMPLE 28

After-Shave Lotion

An anti-inflammation after-shave lotion was prepared as follows:
30 gm of 2-(5'-methylfuryl-2')-4,5-dimethyl-1,3-dioxolane and a solution of:
5 gm of citric acid
30 gm of glycerine in
100 gm of witch hazel, were incorporated into a perfumed 80% alcoholic preparation, so as to produce a total weight of 1000 gm.

EXAMPLE 29

Sun Barrier Cream

A sun barrier cream was prepared as follows:
40 gm of glycerine monostearate
160 gm of beeswax
420 gm of mineral oil
50 gm of ceresine
50 gm of an absorption base prepared from cholesterol, beeswax, stearyl alcohol and Vaseline, and
30 gm of 2-(5'-nitrofuryl-2')-4,4,6-trimethyl-1,3-dioxane
were melted together at a temperature of 65° C. A mixture of:
247 gm of water
13 gm of borax, and
2 gm of methyl para-hydroxybenzoate, heated to the same temperature,
was then incorporated into the warm mixture under vigorous stirring and the cream thus obtained stirred further until it reached room temperature.

EXAMPLE 30

Sun Barrier Emulsion

A sun barrier emulsion was prepared by adding a mixture of:
800 gm of water,
10 gm of glycerine, and
9 gm of triethanolamine,
under vigorous stirring to a mixture (heated to about 80° C) of the following:
20 gm of glycerine monostearate
70 gm of stearic acid
30 gm of oleic acid
20 gm of cetyl alcohol, and
40 gm of 2-(5'-nitrofuryl-2')-1,3-dioxolane.
The lotion thus obtained was stirred until cold.

The emulsion so produced can also be packed in aerosol form by combining it with a propellant in the ratio of 80 parts of lotion to 20 parts of propellant gas.

Any of the other listed anti-inflammatory cyclic 2-furfural-acetal compounds may be employed in place of those actually employed in Example 26 to 30 with comparable results. Similarly other customary pharmaceutical preparations for sunburn protection and anti-inflammation cosmetic preparations may be employed containing from 0.01% to 10% by weight of the anti-inflammatory cyclic 2-furfural-acetal compounds of the invention.

The preceding specific embodiments are illustrative of the practice of the invention. It is to be understood, however, that other expedients known to those skilled in the art or disclosed herein may be employed without departing from the spirit of the invention or the scope of the appended claims.

We claim:
1. A process for the prevention or alleviation of inflammation of the skin consisting essentially of applying to the skin to be protected an anti-inflammatory effective amount of an anti-inflammatory cyclic 2-furfural-acetal compound having the formula

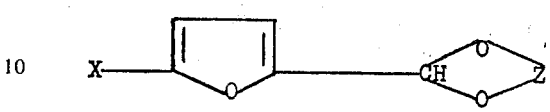

wherein X is selected from the group consisting of hydrogen, lower alkyl and nitro, Z is alkylene having the formula

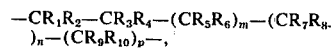

wherein $R_1$, $R_2$, $R_3$, $R_4$, $R_5$ and $R_6$ are each selected from the group consisting of hydrogen, alkyl having 1 to 26 carbon atoms, hydroxyalkyl having 1 to 26 carbon atoms and phenyl, and wherein $R_7$, $R_8$, $R_9$ and $R_{10}$ are each selected from the group consisting of hydrogen and lower alkyl, and $R_1$ and $R_3$ or $R_1$ and $R_5$ taken together are alkylene having 3 to 6 carbon atoms, $m$, $n$ and $p$ are each the integer 0 or 1.

2. The process of claim 1, wherein X is alkyl having 1 to 4 carbon atoms, and $R_7$, $R_8$, $R_9$ and $R_{10}$ are each alkyl having 1 to 4 carbon atoms.

3. The process of claim 1, wherein $R_1$, $R_2$, $R_3$, $R_4$, $R_5$ and $R_6$ are each selected from the group consisting of hydrogen and alkyl having 1 to 16 carbon atoms.

4. The process of claim 1, wherein X is selected from the group consisting of hydrogen, methyl and nitro, wherein $R_1$, $R_2$, $R_3$, $R_4$, $R_5$ and $R_6$ are each selected from the group consisting of hydrogen, methyl, ethyl, propyl, isopropyl, butyl, hexyl, octyl, decyl, dodecyl, tetradecyl, hexadecyl and phenyl, wherein $R_7$ and $R_8$ are each selected from the group consisting of hydrogen and methyl, and wherein $R_1$ and $R_3$ or $R_1$ and $R_5$ taken together are alkylene having 4 carbon atoms; and wherein $m$ and $n$ are each the integer 0 or 1, and $p$ is 0.

5. The process of claim 1 for preventing or alleviating sunburn.

6. An anti-inflammatory cosmetic preparation consisting essentially of from 0.01% to 10% by weight of 2-(5'-nitrofuryl-2')-4-isopropyl-5,5-dimethyl-1,3-dioxane; and the remainder inert cosmetic excipients.

7. An anti-inflammatory cosmetic preparation consisting essentially of from 0.01% to 10% by weight of 2-(5'-nitrofuryl-2')-4,4,6-trimethyl-1,3-dioxane; and the remainder inert cosmetic excipients.

8. An anti-inflammatory cosmetic preparation consisting essentially of from 0.01% to 10% by weight of 2-(5'-nitrofuryl-2')-1,3-dioxolane; and the remainder inert cosmetic excipients.

* * * * *